United States Patent
Zhang et al.

(10) Patent No.: US 10,487,321 B2
(45) Date of Patent: Nov. 26, 2019

(54) METHOD OF EXTRACTION OF GENOMIC DNA FOR MOLECULAR DIAGNOSTICS AND APPLICATION

(71) Applicant: PZM Diagnostics, LLC, Charleston, WV (US)

(72) Inventors: Peilin Zhang, Charleston, WV (US); Lawrence M. Minardi, Charleston, WV (US)

(73) Assignee: PZM DIAGNOSTICS, LLC, Charleston, WV (US)

( * ) Notice: Subject to any disclaimer, the term of this patent is extended or adjusted under 35 U.S.C. 154(b) by 360 days.

(21) Appl. No.: 15/279,948

(22) Filed: Sep. 29, 2016

(65) Prior Publication Data
US 2018/0087047 A1    Mar. 29, 2018

(51) Int. Cl.
*C12N 15/00* (2006.01)
*C12N 15/10* (2006.01)

(52) U.S. Cl.
CPC ................ *C12N 15/1003* (2013.01)

(58) Field of Classification Search
None
See application file for complete search history.

(56) References Cited

U.S. PATENT DOCUMENTS

2008/0287669 A1* 11/2008 Braman ................ C07H 1/00
                                                            536/25.41
2013/0058902 A1* 3/2013 Kishimoto ......... A61K 38/1816
                                                            424/93.7
2013/0137094 A1* 5/2013 Espina ..................... A01N 1/00
                                                            435/6.11
2014/0171433 A1* 6/2014 Burns .................. A61K 31/198
                                                            514/235.8
2018/0360025 A1* 12/2018 Rosin-Arbesfeld .........
                                                            A61K 31/522

OTHER PUBLICATIONS

Molecular Medicine Ireland (hereinafter "MMI"; SOP 3.4 DNA Extraction from Blood, avail at https://brd.nci.nih.gov/brd/sop/download-pdf/161, May 27, 2015.*
Murcia et al., Molecular features of *Mycobacterium avium* human isolates carrying a single copy of IS1245 and IS1311 per genome, FEMS Microbiol Lett. Jul. 2007;272(2):229-37. Epub Jun. 7, 2007.*
Ei-Sayed et al., Genotyping of *Mycobacterium avium* field isolates based on repetitive elements, International Journal of Veterinary Science and Medicine vol. 1, Issue 1, Jun. 2013, pp. 36-42.*

* cited by examiner

*Primary Examiner* — Aaron A Priest
(74) *Attorney, Agent, or Firm* — Andrew D. Wright; Roberts Mlotkowski Safran Cole & Calderon, P.C.

(57) ABSTRACT

Methods and systems for extracting DNA from a sample are provided. A method includes: lysing red blood cells of the sample using a first solution; dissolving lipids of cellular membranes in the sample using a second solution; and releasing DNA of the sample into a buffer using a third solution.

12 Claims, 5 Drawing Sheets
Specification includes a Sequence Listing.

| PCR Primer sequences | |
|---|---|
| IS901F | GGA TTG CTA ACC ACG TGG TG |
| IS901R | GCG AGT TGC TTG ATG AGC G |
| IS1245F | GAG TTG ACC GCG TTC ATC G |
| IS1245R | CGT CGA GGA AGA CAT ACG G |
| 16S-F | GAG GAA GGT GGG GAT GAC G |
| 16S-R | AGG CCC GGG AAC GTA TTC AC |
| IS900F | CTT TCT TGA AGG GTG TTC GG |
| IS900R | GAG GTC GAT CGC CCA CGT GA |
| ITS1 | 5' TCC GTA GGT GAA CCT GCG G 3' |
| ITS2 | 5' GCTGCGTTCTTCATCGATGC 3' |

FIG. 5

METHOD OF EXTRACTION OF GENOMIC DNA FOR MOLECULAR DIAGNOSTICS AND APPLICATION

SEQUENCE LISTING

The instant application contains a Sequence Listing which has been filed electronically in ASCII format and is hereby incorporated by reference in its entirety. Said ASCII copy is named "6219-40005_SequenceListing_ASCII.txt" and is 2,522 bytes in size.

FIELD OF THE INVENTION

The invention generally relates to the field of diagnostics and, more particularly, to methods of extraction of genomic DNA for molecular diagnostics and application.

BACKGROUND

Genomic DNA extraction from various sources of biological material is a first step for molecular analysis for basic and clinical studies in biomedical sciences. How to effectively extract genomic DNA from starting material is of most importance for a success of basic biomedical research and clinical diagnostics. In clinical diagnostics, peripheral venous blood is commonly the starting material, and microbes and infectious agents are commonly the detecting targets. In the cases of bacterial, mycobacterial and fungi, genomic DNA extraction from these sources are problematic, since the presence of a thick cell wall of high content of lipids makes the DNA extraction difficult, if not entirely impossible. Many previously described methods employ physical forces to destroy the cell wall by using glass beads, mechanical homogenizers, and sonication (ultrasound cell membrane disruptor). After the physical disruption of the cell wall, the genomic DNA will be released to the solutions for further purification.

SUMMARY

Aspects of the invention are directed to a chemical method to extract DNA from a starting material of, for example, whole blood. Implementations of the inventive method are simple, easy and fast, and require less than thirty minutes to obtain quality DNA for subsequent molecular analysis.

In an aspect of the invention, there is a method of extracting DNA from a sample. the method includes: lysing red blood cells of the sample using a first solution; dissolving lipids of cellular membranes in the sample using a second solution; and releasing DNA of the sample into a buffer using a third solution.

In another aspect of the invention, there is a method that includes: creating a first composition by combining a sample with a first solution, wherein the first solution comprises a cell lysis buffer; centrifuging the first composition; removing a first supernatant from the centrifuging the first composition; creating a second composition by combining a second solution with a first pellet from the centrifuging the first composition, wherein the second solution comprises an organic solvent; centrifuging the second composition; removing a second supernatant from the centrifuging the second composition; creating a third composition by combining a third solution with a second pellet from the centrifuging the second composition, wherein the third solution comprises a storage buffer; heating the third composition; and centrifuging the third composition.

In another aspect of the invention, there is a system comprising: a first container having a volume of a first solution comprising a cell lysis buffer; a second container having a volume of a second solution comprising an organic solvent; a third container having a volume of a third solution comprising a DNA storage buffer; and instructions that instruct a user how to use the first solution, the second solution, and the third solution to extract DNA from a sample.

BRIEF DESCRIPTION OF THE SEVERAL VIEWS OF THE DRAWINGS

The present invention is described in the detailed description which follows, in reference to the noted plurality of drawings by way of non-limiting examples of exemplary embodiments of the present invention.

FIG. 5 shows PCR primer sequences in accordance with aspects of the invention (SEQ ID NOS 3-10 and 1-2, respectively, in order of appearance).

DETAILED DESCRIPTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

The invention generally relates to the field of diagnostics and, more particularly, to methods of extraction of genomic DNA (Deoxyribonucleic acid) for molecular diagnostics and application. According to aspects of the invention, a three step method may be used to extract genomic DNA from a whole blood sample of a patient. The extracted genomic DNA may then be used for molecular diagnostics, such as PCR (polymerase chain reaction) analysis. Aspects of the invention may include a method of performing the extraction and a kit used for performing the method.

Genomic DNA extraction from biological material is the first step for molecular analysis in biomedical research and clinical application. Depending upon the starting material, DNA extraction can be difficult. Classic DNA extraction methods consist of cell lysis with various detergents, proteinase K enzyme digestion, organic reagents such as phenol/chloroform extraction of proteins, and ethanol precipitation of DNA. Bacteria, mycobacterial and fungi have thick waxy cell wall that are resistant to detergents and various reagents, and traditional methods of DNA extraction give rise to low yield of quality DNA for further analysis. Aspects of the invention use an entirely different chemical method using hypotonic solution, organic reagents and heat denaturation. The inventors have successfully used implementations of the method for DNA preparation and PCR analysis for clinical diagnostics.

Figure 1:
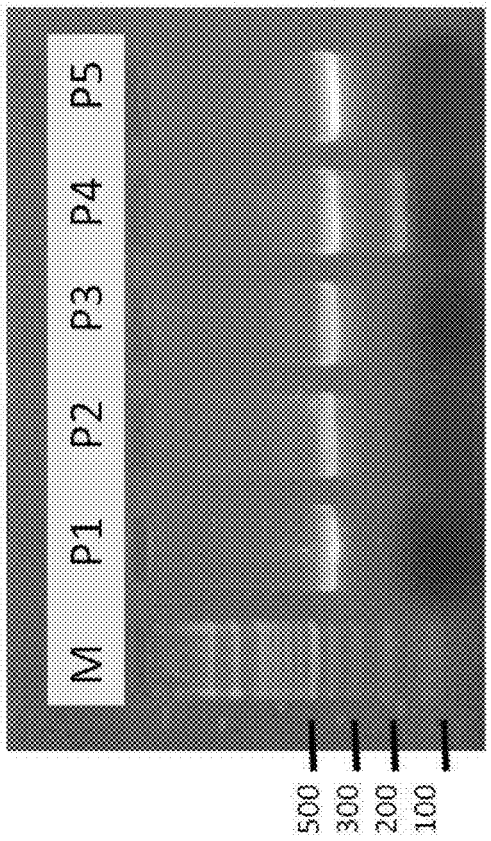
FIG. 1 shows PCR analysis of DNA samples prepared from the blood of Crohn's patients for identification of *Mycobacterium avium* subspecies *paratuberculosis* (MAP) using IS900 primers in accordance with aspects of the invention.

FIG. 1 shows a PCR analysis of DNA samples prepared from the blood of Crohn's patients for identification of *Mycobacterium avium* subspecies *paratuberculosis* (MAP) using IS900 primers. The amplicon at 416 bps is defined by the IS900 primers. M-molecular marker (100 base pair ladder), P1-P5 represent 5 different blood samples prepared by using a test kit (e.g., "The Quick & Easy Genomic DNA Kit by PZM Diagnostics") and method in accordance with aspects of the invention. The IS900 primers shown in FIG. 1 include IS900F and IS900R primers shown in FIG. 5 herein and described in U.S. patent application Ser. No. 14/803,511. The contents of U.S. patent application Ser. No. 14/803,511 are expressly incorporated by reference herein in their entirety. A Sequence Listing of the IS900F and IS900R primers is available in U.S. patent application Ser. No. 14/803,511.

Figure 2:
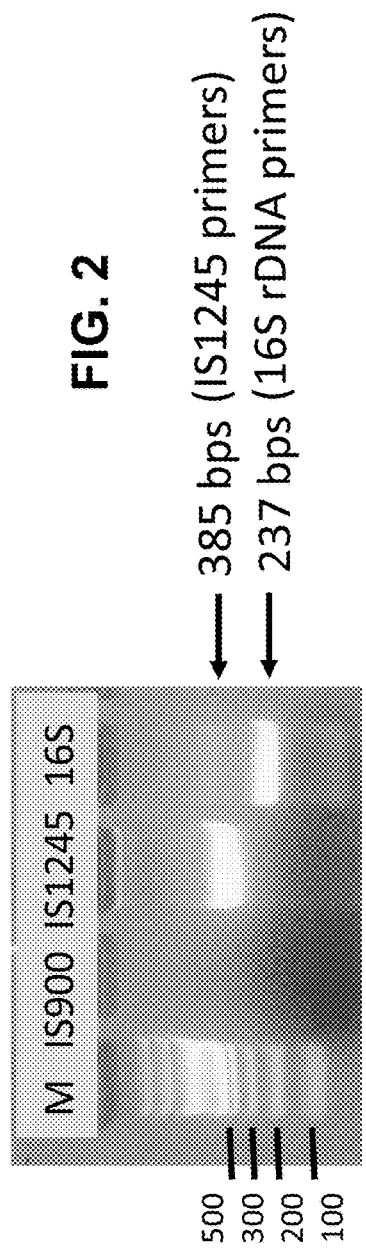
FIG. 2 shows PCR analysis of genomic DNA samples from the blood of one patient with Crohn's disease and *Mycobacterium avium* subspecies *hominissuis* (MAH) by using IS1245 primers and 16S rDNA primers in accordance with aspects of the invention.

FIG. 2 shows PCR analysis of genomic DNA samples from the blood of one patient with Crohn's disease and *Mycobacterium avium* subspecies *hominissuis* (MAH) by using IS1245 primers and 16S rDNA primers. The 385 bps amplicon is defined by the IS1245 primers and the 237 bps amplicon by the 16S rDNA primers. The genomic DNA from the blood of the patient was prepared using a test kit (e.g., "The Quick & Easy Genomic DNA Kit by PZM Diagnostics") and method in accordance with aspects of the invention. M-molecular weight marker (100 bps ladder). The IS1245 primers shown in FIG. 2 include IS1245F and IS1245R primers shown in FIG. 5 herein and described in U.S. patent application Ser. No. 14/803,511. The 16S rDNA primers shown in FIG. 2 include 16S-F and 16S-R primers shown in FIG. 5 herein and described in U.S. patent application Ser. No. 14/803,511. A Sequence Listing of the IS1245F and IS1245R primers and the 16S-F and 16S-R primers is available in U.S. patent application Ser. No. 14/803,511.

Figure 3:
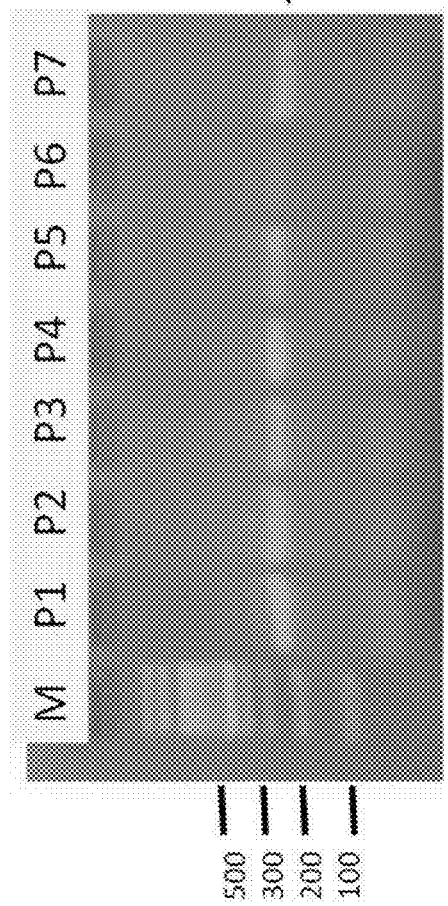
FIG. 3 shows PCR analysis of bacterial DNA using 16S rDNA primers and genomic DNA samples prepared from the blood of seven patients in accordance with aspects of the invention.

FIG. 3 shows a PCR analysis of bacterial DNA using 16S rDNA primers and genomic DNA samples prepared from the blood of seven patients using a test kit (e.g., "The Quick & Easy Genomic DNA Kit by PZM Diagnostics") and method in accordance with aspects of the invention. M-molecular weight marker (100 bps ladder). P1-P7 represent seven different patients, three with Crohn's disease (P1-3), chronic fatigue syndrome (P4), rheumatoid arthritis (P5), multiple sclerosis (P6), and Lyme disease (P7). The 16S rDNA primers shown in FIG. 3 include 16S-F and 16S-R primers shown in FIG. 5 herein and described in U.S. patent application Ser. No. 14/803,511. A Sequence Listing of the 16S-F and 16S-R primers is available in U.S. patent application Ser. No. 14/803,511.

Figure 4:
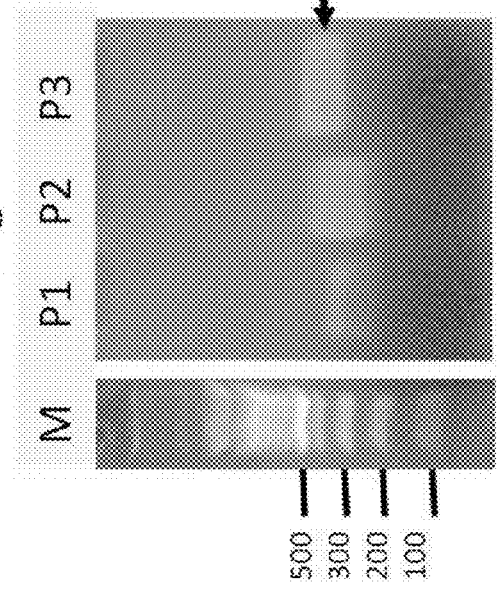
FIG. 4 shows PCR analysis of fungal DNA using ITS1 and ITS2 primers and the genomic DNA from the blood of three separate patients with various clinical diagnosis in accordance with aspects of the invention.

FIG. 4 shows a PCR analysis of fungal DNA using ITS1 and ITS2 primers and the genomic DNA from the blood of three separate patients with various clinical diagnosis using a test kit (e.g., "The Quick & Easy Genomic DNA Kit by PZM Diagnostics") and method in accordance with aspects of the invention. M-molecular weight marker (100 bps ladder). P1-3, three patients with various clinical diseases and fungemia. The ITS1 and ITS2 primers are as follows:

```
                                              (SEQ ID NO: 1)
     ITS1 5' TCC GTA GGT GAA CCT GCG G 3'

(SEQ ID NO: 2)
     ITS2 5' GCTGCGTTCTTCATCGATGC 3'
```

FIG. 5 shows PCR primer sequences in accordance with aspects of the invention.

Figure 6:
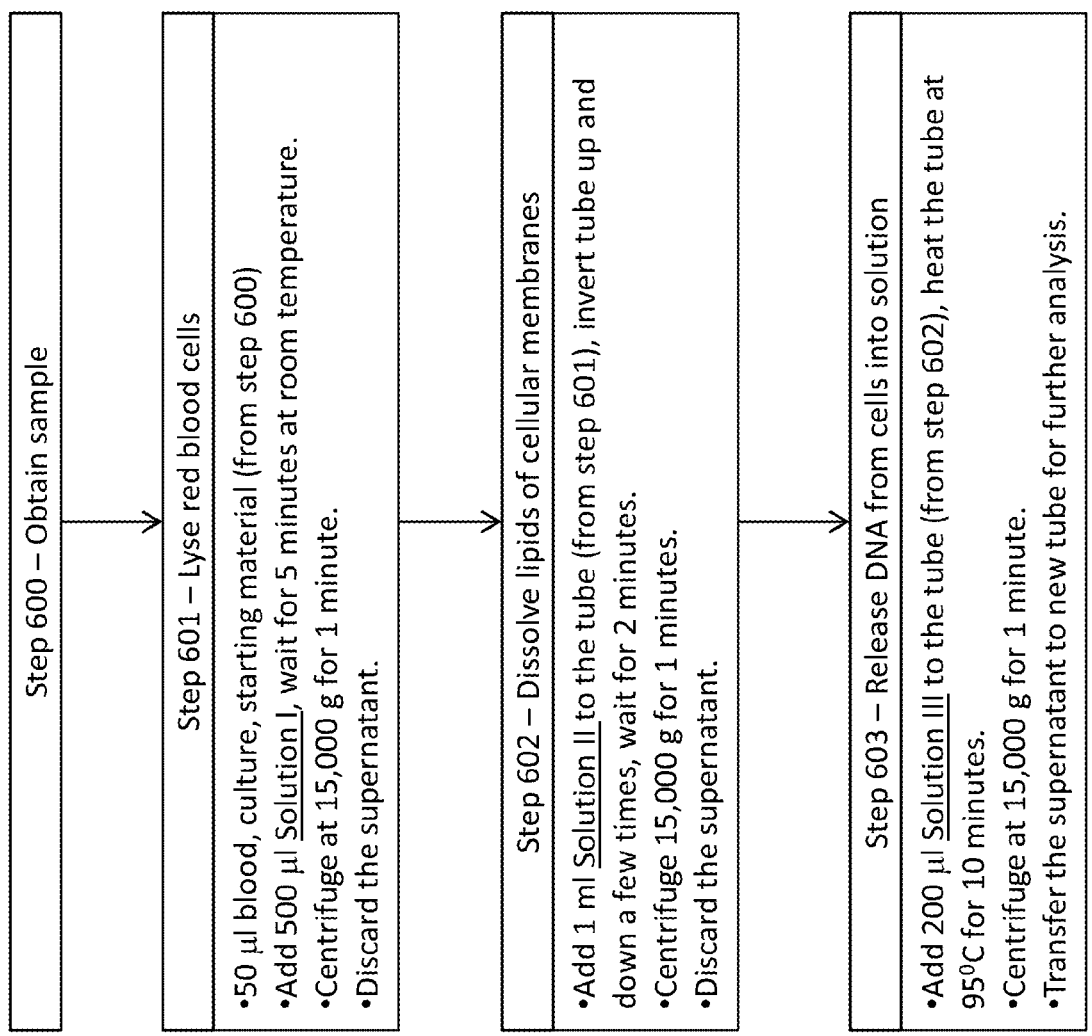
FIG. 6 shows a flow chart of a method of genomic DNA extraction in accordance with aspects of the invention.

FIG. 6 shows a flow chart of a method of genomic DNA extraction in accordance with aspects of the invention. Step 600 includes obtaining a sample from an individual (e.g., a patient). In a preferred embodiment, the sample is whole blood of the individual, although the invention is not limited to use with whole blood and can instead employ other starting materials such as bacterial/mycobacterial/fungi/yeast culture, or other body fluids of the individual such as pleural fluid, ascites, or vitreous fluid.

At step 601, red blood cells of the sample are lysed using a cell lysis buffer. In embodiments, step 601 includes creating a first composition by combining a volume of a first solution (Solution I) and the sample (from step 600), and centrifuging the first composition. Step 601 may include removing the supernatant after the centrifuging.

In a preferred embodiment, step 601 includes: using a 1.5 ml Eppendorf tube (microcentrifuge tube) with a sample of about 50 µl (microliter) whole blood, bacterial/mycobacterial/fungi/yeast culture, or other body fluids such as pleural fluid/ascites/vitreous fluid; adding about 500 µl of Solution I to the tube; mixing this first composition (the sample and Solution I) in the tube; incubating the first composition in the tube, e.g., at room temperature for 5 minutes; and centrifuging the first composition in the tube, e.g., at about 15,000 g (12,000 rpm) for about one minute at room temperature. Step 1 may be repeated as necessary to remove red blood cells from the sample.

At step 602, lipids within cellular membranes of remaining cells are dissolved using an organic solvent. In embodiments, step 602 includes creating a second composition by combining a volume of a second solution (Solution II) and the pellet that remains after the centrifuging at step 601. Step 602 may include centrifuging the second composition and removing the supernatant after the centrifuging.

In a preferred embodiment, step 602 includes: adding about 1 ml of Solution II to the tube containing the pellet after step 601, and mixing (gently) this second composition in the tube. In the event there is a visible pellet at the bottom of the tube, then flip the tube gently to disperse the cell pellet. In the preferred embodiment, step 602 also includes: incubating the second composition in the tube, e.g., at room temperature for about two minutes; centrifuging the second composition in the tube, e.g., at about 15,000 g (12,000 rpm) for about one minute; discarding the supernatant from the tube after the centrifuging; and placing the uncapped tube (containing a pellet) upside down on a fresh paper towel for about five minutes.

At step 603, DNA from the cells is released into solution using a DNA storage buffer. In embodiments, step 603 involves creating a third composition by combining a volume of a third solution (Solution III) and the pellet that remains after the centrifuging at step 602. Step 603 may include centrifuging the third composition. The supernatant that results from the centrifuging at step 603 includes extracted DNA from the original sample (from step 600) and can subsequently be used in molecular diagnostics such as PCR analysis In a preferred embodiment, step 603 includes: adding about 200 μl of Solution III to the tube containing the pellet after step 602; heating this third composition, e.g., by placing the tube containing the third composition on a heating block at about 95° C. for about ten minutes; centrifuging the third composition in the tube, e.g., at about 15000 g for about one minute; and transferring the supernatant to a fresh tube for subsequent analysis, such as PCR or RT-PCR (Reverse transcription polymerase chain reaction). The resultant DNA aliquot can be stored at −200° C. for minimally one year. In embodiments, the method may include, after step 603, a step of performing an analysis using the supernatant from step 603. The analysis may comprise, for example, PCR or RT-PCR analysis.

In embodiments, Solution I is a cell lysis buffer, Solution II is an organic solvent, and Solution III is a DNA storage buffer. In a preferred embodiment, Solution I is a red cell lysis buffer and is composed of: Ammonium chloride 0.8%, Sodium bicarbonate 0.08%, EDTA 0.04% (e.g., disodium EDTA, e.g., Ethylenediaminetetraacetic acid), remainder water. In a preferred embodiment, Solution II is composed of: Acetone (commercial grade). In a preferred embodiment, Solution III is a TE buffer having a pH of 7.6 and is composed of: 10 mM Tris-HCL pH 7.6, 1 mM EDTA pH 7.6, remainder water (Tris refers to Tris(hydroxymethyl) aminomethane).

Figure 7:
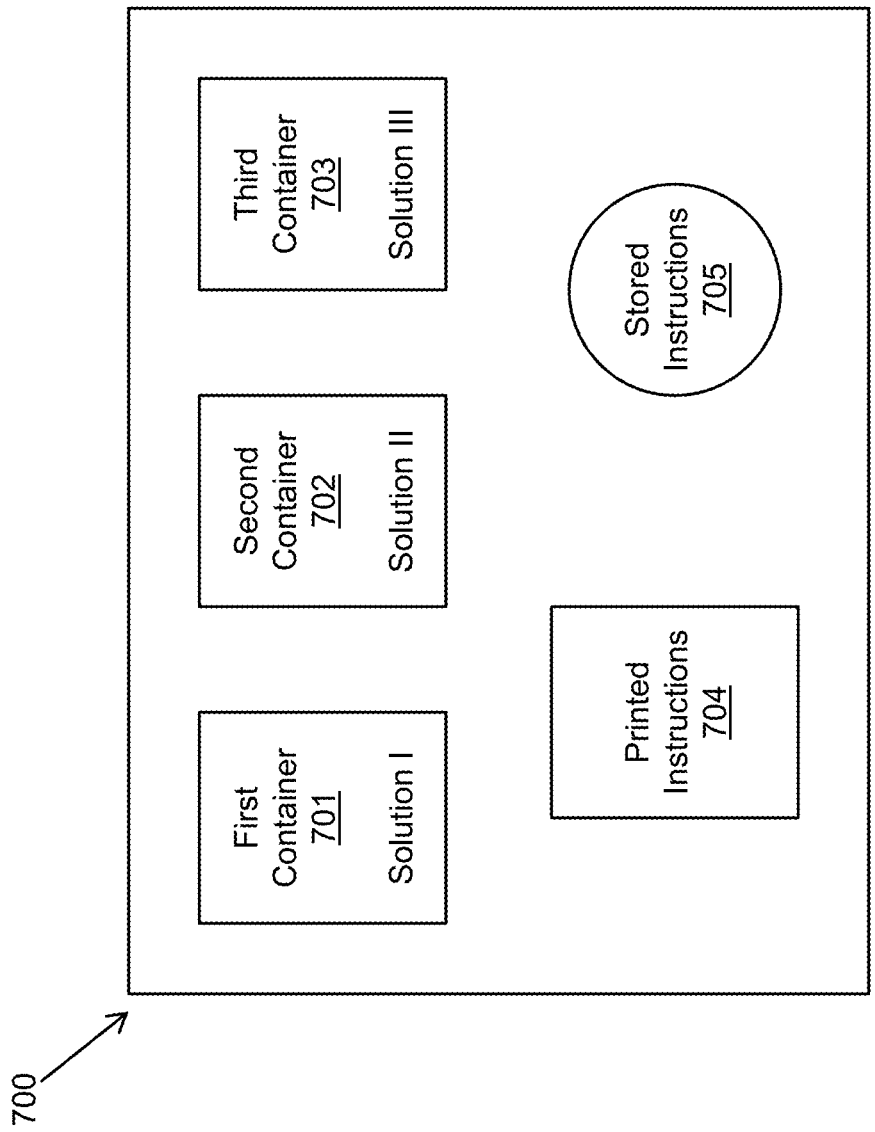
FIG. 7 shows a kit in accordance with aspects of the invention.

The following steps can be used as instructions for an implementation of the method of FIG. 6. The steps may be included as instructions in a system such as a kit 700 as illustrated in FIG. 7. The kit 700 may include a predetermined volume (e.g., 50 ml) of Solution I in a first container 701, a predetermined volume (e.g., 50 ml) of Solution II in a second container 702, and a predetermined volume (e.g., 50 ml) of Solution III in a third container 703. The containers 701-703 may be any desired containers suitable for storing the solutions held therein (e.g., bottle, jar, etc.). The kit 700 may include a printed copy 704 and/or an electronic copy 705 (e.g., stored on computer readable media such as a floppy disk, CD, flash drive, etc.) of the ordered instructional steps, which may be as follows:

1. Take 100 μl whole blood (bacterial/fungal/mycobacterial liquid culture) with micropipette, and transfer blood to a 1.5 ml microcentrifuge tube.
2. Add 500 μl Solution I, mix thoroughly by inverting the tube several times, let it sit at room temperature for 5 minutes.
3. Spin the tube at 15,000 g (12,000 rpm) for 1 minute in a microcentrifuge at room temperature.
4. Discard the supernatant to a biohazard container (the supernatant from the blood should be dark red, if not red, re-mix the solution and wait for another 5 minutes, spin again). A small visible pellet should be at the bottom of the tube. There will be some liquid (20 μl) left at the bottom of the tube, do not try to remove all liquid from the tube.
5. Flip the bottom of the tube several times to mix the cell pellet with the remaining liquid until no visible clumps.
6. Add 1 ml Solution II, mix thoroughly. Make sure the cap is tight.
7. Spin the tube at 15,000 g (12,000 rpm) for 1 minute. Discard the supernatant, let the tube sit on a paper towel upside down for 2 minutes to dry.
8. Resuspend the cell pellet in 200 μl Solution III. Close the cap of the tube, and heat the tube on a heating block at 95° C. for 15 minutes with intermittent flipping of the tube to better dissolve the pellet.
9. Chill the tube on ice for 2 minutes, spin the tube at 15,000 g (12,000 rpm) for 1 minute. Transfer the supernatant to another microfuge tube.
10. Use 0.5 μl or less for PCR analysis (no more than 1 μl), and 1-2 μl for RT-PCR.

Implementations of the inventive method described herein are suitable for extraction of genomic DNA from various sources of biomaterial. In embodiments, the method uses a lipid extractor such as Solution II (Acetone) to dissolve all the lipids within the cellular membranes including nuclear membrane so that all the remaining cellular components will be soluble in aqueous solution such as biological buffers. The method is especially suitable for genomic DNA extraction from bacterial, mycobacteria and fungi. Bacteria and mycobacteria consist of thick cell wall with heavy components of lipids and fatty acids which makes conventional DNA extraction methods very difficult if not impossible to work. Fungal cell wall is thick and rigid, and removal of lipid from the cell wall using organic solvents such as acetone extraction, according to aspects of the invention, makes it easier to extract high quality DNA for subsequent biomedical analysis. Such a method can also be applied to extraction of RNA and cellular proteins from the same starting biomaterial.

The inventors have successfully used embodiments of the method described herein to extract total genomic DNA from the peripheral blood for detection of the presence of bacterial DNA, mycobacterial DNA, and fungal elements. The extracted genomic DNA was further analyzed by subsequent polymerase chain reaction (PCR) for identification of pathogenic agents within the blood. As shown in FIGS. 1-4, *Mycobacterium avium* subspecies *paratuberculosis* (MAP), *Mycobacterium avium* subspecies *hominissuis* (MAH), various bacteria and various fungi have been identified from the blood of patients with various disease processes including Crohn's disease, multiple sclerosis, rheumatoid arthritis, and the mixed connective tissue diseases. PCR analysis for bacteria was using universal 16S rDNA primers. PCR analysis for MAP was using IS900 primers, MAH was using IS1245 primers, and all fungal microorganisms were using ITS1 and ITS2 primers as previously published. The PCR amplicons can be further determined by direct DNA sequencing.

Genomic DNA extraction from various sources of biological material remains to be a first step for successful analysis in biomedical research and clinical applications. Traditionally the genomic extraction process is lengthy using mechanical forces, proteinase K digestions, organic solvent extraction of proteins and precipitation of the DNA/RNA. These processes take much longer time (24 hours with over-night proteinase K digestion), and the mechanical process employs expensive instrumentation. In contrast, DNA extraction using a method and kit according to aspects of the invention takes less than 30 minutes with Solutions I, II and III with comparable results.

An important issue for microbial research and clinical application is contamination of bacterial/microbial DNA from unwanted sources. Implementations of the inventive method and kit can be well-controlled to ensure no microbial DNA contamination from the kit components. There is no additional step or material in the process, thus eliminating the potential of contamination.

The inventors have developed a genomic DNA extraction kit using three simple steps with simple biological solutions. Implementations of the inventive kit can be used for a variety of starting material for genomic DNA extraction and subsequent molecular PCR analysis. Implementations of an inventive method may include three simple steps with three simple reagents: Solution I being a cell lysis buffer; Solution II being an organic solvent; and Solution III being a DNA storage buffer.

It is noted that the foregoing examples have been provided merely for the purpose of explanation and are in no way to be construed as limiting of the present invention.

While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A method of extracting DNA from a sample, the method comprising:
   lysing red blood cells of the sample in an aqueous cell lysis buffer solution comprising Ammonium chloride, Sodium bicarbonate and Ethylene Diammine TetraAcetate (EDTA), and then centrifuging the sample and removing the supernatant;
   dissolving lipids of cellular membranes in the pellet in acetone, then separating the acetone from the pellet; and
   releasing DNA of the sample into a storage buffer solution to obtain a solution comprising extracted DNA.

2. The method of claim 1, wherein in the cell lysis buffer the amount of Ammonium chloride is 0.8%, the amount of Sodium bicarbonate is 0.08%, and the amount of EDTA is 0.04%.

3. The method of claim 1, wherein the storage buffer solution consists of 10 mM Tris-HCL pH 7.6, 1 mM EDTA, and water.

4. The method of claim 1, further comprising performing an analysis using the solution comprising extracted DNA.

5. The method of claim 4, wherein the analysis comprises one of PCR analysis and RT-PCR analysis.

6. The method of claim 4, wherein the analysis is configured to detect one of: *Mycobacterium avium* subspecies *paratuberculosis* (MAP); *Mycobacterium avium* subspecies *hominissuis* (MAH); bacteria, and fungi.

7. A method for obtaining DNA from a blood sample, comprising:
   creating a first composition by combining a sample with an aqueous cell lysis buffer that comprises Ammonium chloride, Sodium bicarbonate and Ethylene Diammine TetraAcetate (EDTA);
   centrifuging the first composition;
   removing a first supernatant resulting from the centrifuging the first composition;
   creating a second composition by combining a first pellet from the centrifuging the first composition with acetone;
   centrifuging the second composition;
   removing a second supernatant resulting from the centrifuging the second composition;
   creating a third composition by combining a storage buffer comprising Tris and EDTA with a second pellet from the centrifuging the second composition;
   heating the third composition;
   centrifuging the third composition; and
   removing a third supernatant comprising said DNA.

8. The method of claim 7, wherein:
   the amount of Ammonium chloride in the cell lysis buffer is 0.8%.

9. The method of claim 7, wherein the sample is one of: whole blood, bacterial culture, mycobacterial culture, fungi culture, yeast culture, pleural fluid, ascites, and vitreous fluid.

10. The method of claim 7, further comprising:
    removing the third supernatant resulting from the centrifuging the third composition; and
    performing a molecular analysis using the third supernatant.

11. The method of claim 10, wherein the molecular analysis comprises one of:
    PCR analysis using IS900 primers configured to identify *Mycobacterium avium* subspecies *paratuberculosis* (MAP);
    PCR analysis using at least one of IS1245 primers and 16S rDNA primers configured to identify *Mycobacterium avium* subspecies *hominissuis* (MAH);
    PCR analysis using 16S rDNA primers configured to identify bacteria; and
    PCR analysis using ITS1 and ITS2 primers configured to identify fungi.

12. The method of claim 1, in which the DNA is isolated from bacteria or *mycobacterium* or fungi in the sample.

* * * * *

SEQUENCE LISTING

```
<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tccgtaggtg aacctgcgg                                                   19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gctgcgttct tcatcgatgc                                                  20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggattgctaa ccacgtggtg                                                  20

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcgagttgct tgatgagcg                                                   19

<210> SEQ ID NO 5
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 5
gagttgaccg cgttcatcg                                                   19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgtcgaggaa gacatacgg                                                   19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaggaaggtg gggatgacg                                                   19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aggcccggga acgtattcac                                                  20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctttcttgaa gggtgttcgg                                                  20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gaggtcgatc gcccacgtga                                                  20
```